United States Patent
Gergely et al.

(10) Patent No.: US 8,513,481 B2
(45) Date of Patent: Aug. 20, 2013

(54) WOUND DRESSING WITH HIGH LIQUID HANDLING CAPACITY

(75) Inventors: Ann-Britt Gergely, Molndal (SE); Bengt Netsner, Lindome (SE); Anders Dahlberg, Olofstorp (SE); Eva-Karin Daun, Lerum (SE)

(73) Assignee: Molnlycke Health Care AB, Gothenburg (SE)

( * ) Notice: Subject to any disclaimer, the term of this patent is extended or adjusted under 35 U.S.C. 154(b) by 8 days.

(21) Appl. No.: 13/378,490

(22) PCT Filed: May 11, 2010

(86) PCT No.: PCT/SE2010/050513
§ 371 (c)(1),
(2), (4) Date: Dec. 15, 2011

(87) PCT Pub. No.: WO2010/147533
PCT Pub. Date: Dec. 23, 2010

(65) Prior Publication Data
US 2012/0095380 A1    Apr. 19, 2012

(30) Foreign Application Priority Data
Jun. 15, 2009  (SE) ........................................ 0950460

(51) Int. Cl.
*A61F 13/00*   (2006.01)
(52) U.S. Cl.
USPC .............................................. 602/42; 602/54
(58) Field of Classification Search
USPC ............... 602/41–54; 128/888–889; 604/20, 604/304
See application file for complete search history.

(56) References Cited

U.S. PATENT DOCUMENTS

| 4,203,435 | A |   | 5/1980 | Krull |
| 4,499,896 | A | * | 2/1985 | Heinecke .................... 602/47 |
| 4,605,402 | A |   | 8/1986 | Iskra |
| 5,167,613 | A |   | 12/1992 | Karami |
| 5,409,742 | A | * | 4/1995 | Arfsten et al. ............. 427/555 |
| 5,593,395 | A | * | 1/1997 | Martz ........................ 604/304 |
| 6,051,747 | A |   | 4/2000 | Lindqvist |
| 2009/0216168 | A1 |   | 8/2009 | Eckstein |
| 2009/0227935 | A1 | * | 9/2009 | Zanella et al. ............... 604/20 |

FOREIGN PATENT DOCUMENTS

| EP | 0300620 | 1/1989 |
| WO | WO 2000/051650 | 9/2000 |
| WO | WO 02/05737 | 1/2002 |
| WO | WO 2008/055586 | 5/2008 |

OTHER PUBLICATIONS

International Search Report issued on Oct. 1, 2010 for International Application No. PCT/SE2010/050513 (WO 2010/147533), which was filed on May 11, 2010 [Inventor—Gergely; Applicant—Molnlycke Health Care AB] [4 pages].
Written Opinion issued on Oct. 1, 2010 for International Application No. PCT/SE2010/050513 (WO 2010/147533), which was filed on May 11, 2010 [Inventor—Gergely; Applicant—Mölnlycke Health Care AB] [4 pages].
International Preliminary Report on Patentability issued on Dec. 16, 2011 for International Application No. PCT/SE2010/050513 (WO 2010/147533), which was filed on May 11, 2010 [Inventor—Gergely; Applicant—Molnlycke Health Care AB] [5 pages].

* cited by examiner

*Primary Examiner* — Michael A. Brown
(74) *Attorney, Agent, or Firm* — Ballard Spahr LLP

(57) ABSTRACT

A wound dressing with a wound pad and a layer of vapor-permeable material arranged on top of the wound pad and extending peripherally outside the wound pad is described, wherein at least that part of the vapor-permeable layer extending peripherally outside the wound pad is coated with adhesive, and wherein the wound pad includes a liquid-retaining and liquid-transporting layer, and an upper distributing layer and lower distributing layer which bear against the top and underside, respectively, of the liquid-retaining and liquid-transporting layer.

16 Claims, 1 Drawing Sheet

WOUND DRESSING WITH HIGH LIQUID HANDLING CAPACITY

CROSS REFERENCE TO RELATED APPLICATIONS

The present application is a National Phase Application of International Application No. PCT/SE2010/050513, filed May 11, 2010, which claims priority to Swedish Patent Application No. 0950460-6, filed Jun. 15, 2009, which applications are incorporated herein fully by this reference.

TECHNICAL FIELD

The present invention relates to a wound dressing with a wound pad that includes a liquid-transporting first layer, a liquid-retaining and liquid-transporting second layer, which is arranged on top of the first layer, and a distributing layer arranged between the first layer and the second layer, and with a layer of vapour-permeable material which is arranged on top of the second layer and which extends peripherally outside the wound pad, wherein at least that part of the vapour-permeable layer extending peripherally outside the wound pad is coated with adhesive.

BACKGROUND ART

A dressing of this kind is known in the form of Mepilex Border®, which is sold by Mölnlycke Health Care AB, Gothenburg, Sweden. A great advantage of this dressing is that, because of the way it controls the liquid from the wound, it can be left in place on a wound for quite a long time without needing to be changed. From the point of view of liquid handling, the dressing does not need to be changed before it leaks. It is well known that changing a dressing tends to disrupt the healing of a wound, and this means that the fewer changes of dressings that are needed the better. Of course, fewer changes of dressings also mean less work for nursing personnel and also cost savings.

The object of the present invention it to increase the ability of such a dressing to handle liquid from wounds, such that it can be left in place on the wound for a longer period of time or is able to handle more liquid during the same period of time.

DISCLOSURE OF THE INVENTION

This object is achieved by means of a wound dressing with a wound pad and with a layer of vapour-permeable material arranged on top of the wound pad and extending peripherally outside the wound pad, wherein at least that part of the vapour-permeable layer extending peripherally outside the wound pad is coated with adhesive, characterized in that the wound pad includes a liquid-retaining and liquid-transporting layer, and an upper distributing layer and lower distributing layer which bear against the top and underside, respectively, of the liquid-retaining and liquid-transporting layer. The upper distributing layer increases the amount of liquid that leaves the dressing by evaporation and therefore the amount of liquid that can be handled by the dressing. A dressing according to the invention can be left in place on a wound for a longer period of time than said known dressing without having to be changed, or it can handle more liquid during the same period of time that the known dressing is intended to remain in place on a wound.

According to a first preferred embodiment, the wound pad includes a liquid-transporting first layer, which is arranged under the lower of the distributing layers and bears thereon. The layers of the wound pad are preferably connected adhesively or mechanically to one another, and the layer of vapour-permeable material is connected adhesively to the wound pad. The layers of the wound pad can instead be connected to one another with the aid of heat and pressure or with the aid of ultrasound. This ensures that capillary forces and wetting forces inside the dressing have the intended effect.

Moreover, the liquid-retaining and liquid-transporting second layer is composed of one or more plies containing a mixture of hydrophilic or hydrophilized absorbent fibres and superabsorbents in powder form, fibre form or other form. Binding fibres can be mixed into the liquid-retaining and liquid-transporting second layer. In this way, it is possible to achieve a desired and suitable balance between the properties of this layer in respect of transport and retention of liquid.

The liquid-retaining and liquid-transporting layer in this case advantageously has capillaries of different sizes, wherein the capillaries in contact with the second distributing layer are smaller than the capillaries in other areas of the liquid-retaining and liquid-transporting second layer. Moreover, the proportion of superabsorbents in the mixture of absorbent fibres and superabsorbents is greater in an upper part of the liquid-transporting and liquid-retaining layer than in a lower part thereof.

One of the distributing layers or both of the distributing layers can be integrated in the liquid-retaining and liquid-transporting layer.

In one variant, the liquid-retaining and liquid-transporting second layer can be composed of polymer foam with or without admixture of superabsorbents.

The liquid-transporting first layer can advantageously be composed of a polymer foam.

The distributing layers can be composed of tissue, hydrophilic nonwoven material or polymer foam.

The vapour-permeable layer is preferably composed of a polymer film that has a vapour permeability greater than 2000 $g/m^2$ per 24 hours, measured according to ASTM D 6701.

The wound pad can be coated on its underside with a liquid-permeable layer of adhesive, wherein the adhesive coating on the liquid-transporting first layer can be discontinuous and composed of a silicone adhesive placed on a perforated support, which in turn is secured to the underside of the wound pad and to the vapour-permeable film in the part thereof extending peripherally outside the wound pad.

BRIEF DESCRIPTION OF THE DRAWINGS

The invention will now be described with reference to the attached drawing, in which.

DESCRIPTION OF EMBODIMENTS

Figure 1:
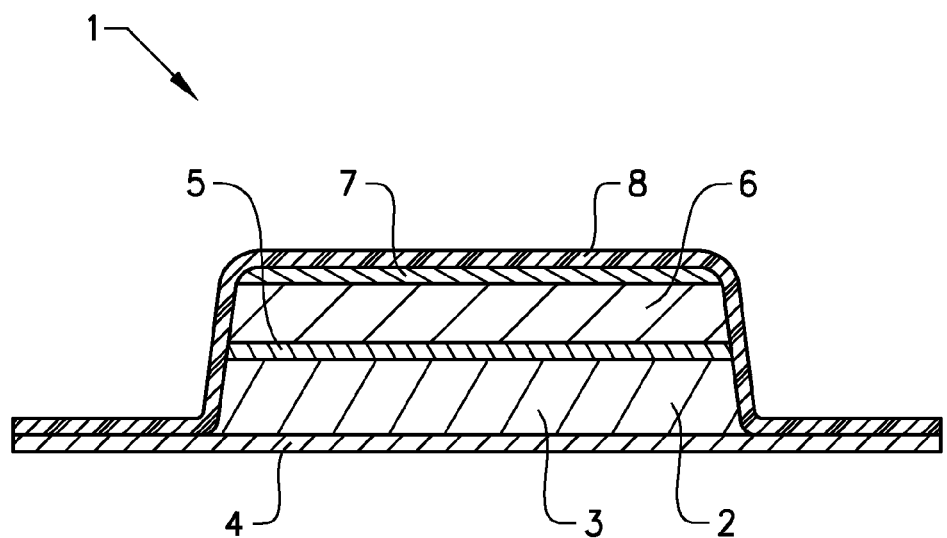
FIG. 1 shows a schematic cross section through a wound dressing according to a first preferred embodiment of the invention.

FIG. 1 shows a first preferred embodiment of a wound dressing 1 according to the invention. The dressing 1 comprises a wound pad 2, which is coated on its underside with a layer 4 of skin-compatible adhesive. The term "underside" refers to the lower face of the wound pad 2 in FIG. 1 which during use of the dressing will lie nearest to a wound.

It will be appreciated that, depending on where it is to be applied to the body, a dressing may be positioned in such a way that the underside shown in FIG. 1 may be facing upwards for example. The terms "over", "under", "upper", "lower", "on top of" and similar references to position used in the description and in the claims refer to the relative location of various components with respect to one another when the dressing is in the situation shown in FIG. 1.

A layer 8 of vapour-permeable material extends on top of the wound pad 2 and peripherally outside the wound pad.

In the preferred embodiment, the layer 4 is composed of a support in the form of a perforated polyurethane layer coated with silicone adhesive covering the areas between the perforations, which layer also extends over that part of the layer 8 extending peripherally outside the wound pad 2. The perforated support layer is preferably glued to the wound pad 2 and to the cover layer 8.

The wound pad 2 includes a liquid-transporting first layer 3 on the top face of which a first distributing layer 5 extends. Arranged on top of the latter layer there is a liquid-retaining and liquid-transporting layer 6. Finally, the wound pad 2 has a second distributing layer 7 arranged on the top face of the liquid-retaining and liquid-transporting layer 6.

Distributing layer means a layer of absorbent material with a thickness of less than 5 mm, preferably of less than 3 mm, having the ability to distribute absorbed liquid in directions at right angles to the direction of thickness.

As has already been mentioned, a cover layer 8 of vapour-permeable polymer film extends on the top face of the second distributing layer and over the side edges of the layers 3-7, and it also extends outside the peripheries of these layers at the level of the adhesive layer 4. The polymer film 8, at least on the underside of the part extending outside the peripheries of the absorbent layers 3-7, is coated with adhesive which, as is shown in FIG. 1, can represent a continuation or part of the adhesive layer 4.

The adhesive layer 4 in the present dressing 1 has two functions. First, it is intended to prevent the wound pad 2 from becoming caught in the wound and, second, it is intended to ensure that the dressing sits firmly on the skin. Moreover, it must of course allow the wound pad to absorb liquid from the wound. The adhesive coating 4 must therefore be liquid-permeable and, for this reason, is arranged discontinuously by the presence of the pattern of perforations.

Another possibility would be to apply an adhesive coating that is itself liquid-permeable, or to do without an adhesive coating on the underside of the wound pad if the wound pad 2 has little tendency to become caught in the wound. However, the underside of the cover layer 8 must always be provided with an adhesive coating, at least in the part extending peripherally outside the wound pad.

It is of course also possible to arrange a layer of bicomponent fibres for example, or a net or a perforated film of polymer material with little tendency to become caught in wounds, between the wound pad 2 and a wound bed, e.g. if the adhesive that is used to secure the dressing to the skin has a tendency to become caught in wounds.

The adhesive coating 4 can be composed of any skin-compatible adhesives known for use in wound dressings. However, soft skin-compatible adhesives are preferred, e.g. polyacrylates or silicone adhesive. A great advantage of soft adhesives is that they can normally be removed from the skin without damaging it. Silicone adhesive is particularly preferred since it additionally has the property whereby the adherence to skin does not appreciably increase over time, which is advantageous especially for dressings that are designed to remain in place on a wound for a long period of time, say for several days. Addition-curing RTV (Room Temperature Vulcanizing) silicone systems, which crosslink after admixture and form a self-adhesive elastomer, are examples of suitable adhesives. EP 0 300 620 A1 gives examples of silicone systems of this kind.

Wacker SilGel 612 is a commercially available RTV silicone system from Wacker-Chemie GmbH, Munich, Germany. By varying the proportions between the two components included in this system, it is possible to vary the softness and level of adherence of the elastomer that is formed. This silicone system is particularly suitable for the adhesive coating 4.

Other examples of soft silicone elastomers are NuSil MED-6340, NuSil MED3-6300, NuSil MED12-6300 from NuSil Technology, Carpintieria, USA and Dow Corning Corporation, Midland, USA.

A hot-melt adhesive similar to Dispomelt® 70-4647 from National Starch and Chemical Company, Bridgewater, N.J., USA can also be used.

The purpose of the first layer 3 of liquid-transporting material is to take up excess liquid from a wound as quickly as possible. For this reason, it should lie near the wound bed, which means that the adhesive layer 4 should be thin.

The layer 3 can advantageously be composed of an absorbent foam material, e.g. a polyurethane foam (see U.S. Pat. No. 6,051,747 for example). Absorbent materials other than foam material can also be used, for example fibre material based on cellulose fibres or other absorbent fibres.

The first distributing layer 5 is intended to drain absorbed liquid from the layer 3 and for this reason has capillaries that are smaller than the capillaries in the layer 3. This means that the flow of liquid in the first layer 3 is substantially vertical when the dressing, during use, is positioned in the manner shown in FIG. 1 and after absorbed liquid has reached the top face of the layer 3. This in turn reduces the risk of liquid absorbed in the layer 3 flowing out to the sides from the lower edge of the layer 3 and under the plastic film 8, which also means that the risk of wound exudate damaging fresh skin is reduced to a corresponding degree.

Another purpose of the first distributing layer 5 is to ensure that liquid absorbed from the layer 3 is distributed sideways. By virtue of the fact that the capillaries in the thin distributing layer 5 are mainly horizontal and are smaller than the capillaries in the layer 3, the liquid transport in the sideways direction takes place to a greater extent in this layer than in the first layer 3 of absorbent material.

The distributing layer 5 is preferably composed of fibre-based material containing hydrophilic or hydrophilized fibres, such as tissue or nonwoven material made up of or containing pulp fibres or cellulose-based fibres, e.g. rayon, or other absorbent fibres, e.g. cotton fibres. In such material, many of the capillaries run horizontally. Other materials too can conceivably be used as distributing layer, e.g. woven or knitted textile material. An example of a suitable material for the distributing layer 5 is Fibrella 2000 from Suominen Corp., Tampere, Finland, with a weight per unit area of 30-50 g/m². It is also conceivable to use thin polymer foam materials as distributing layer.

The liquid-retaining and liquid-transporting layer 6 must, on the one hand, have a high retention capacity, i.e. must ensure that liquid absorbed from the wound is not returned from the dressing to the wound bed in the event of external pressure, and, on the other hand, must be able to transport liquid from the first distributing layer to the second distributing layer. By virtue of the presence of the first distributing layer 5, a large surface area of the layer 6 comes quickly into contact with absorbed liquid, for which reason a large part of the layer 6 will be involved in transporting absorbed liquid to the top face of the layer 6 and thereby to the second distributing layer 7. Transport of liquid from the first distributing layer 5 to the liquid-retaining and liquid-transporting layer 6 will therefore take place immediately after the first distributing layer 5 begins to suck liquid from the underlying layer 3. In the embodiment shown, the liquid-retaining and liquid-transporting layer 6 has smaller capillaries than the liquid-transporting layer 3. In this way, the suction force of the capillaries in the layer 6 is greater than the suction force of the capillaries in the layer 3, which means that the layer 6, not the layer 3, is first to suck liquid from the first distributing layer 5.

In the preferred embodiment, the liquid-retaining and liquid-transporting layer 6 is composed of a mixture of fibres and superabsorbents, e.g. polyacrylates in powder form, fibre form or other form. The fibres can be composed of hydrophilic or hydrophilized absorbent fibres, e.g. viscose fibres, cotton fibres, etc., and binding fibres, e.g. synthetic fibres of thermoplastic material, e.g. polyester. In such a mixture, the absorbent fibres serve for the liquid transport and the superabsorbents serve to increase the liquid retention capacity under the effect of pressure. By suitable mixing, it is possible to achieve an optimal balance between the demands for retention capacity and transport capacity. Moreover, the liquid-retaining and liquid-transporting layer 6 can be composed of two or more plies of different mixtures of fibres and superabsorbents. For example, the liquid-retaining and liquid-transporting layer can be made up of three such layers, in which the proportion of superabsorbents is greatest in the middle ply. The proportion of superabsorbents in the mixture of absorbent fibres and superabsorbents is expediently 5-60% by weight.

The liquid-retaining and liquid-transporting layer 6 can also be made up of the same material as the lower layer 3 with or without admixture of superabsorbent particles. Foam materials other than polyurethane can also be used for the layers 3 and 6.

The second distributing layer 7 sucks liquid from the liquid-retaining and liquid-transporting layer 6 as soon as liquid absorbed in this layer 6 reaches the top face of the liquid-retaining and liquid-transporting layer 6. To accelerate the transport of liquid to the top face of the liquid-retaining and liquid-transporting layer 6, the capillaries in this layer can have a size gradient in which the size decreases in the upward direction.

The second distributing layer 7 can be made of the same material as the first distributing layer 5. An example of a suitable material is Fibrella 2000.

Liquid that has been absorbed in the distributing layer 7 will evaporate through the vapour-permeable polymer film 8. It has been found that the evaporation rate, i.e. the amount of vapour transported through the vapour-permeable film, increases in line with the concentration of liquid in the area under the film and also when the liquid is in contact with the underside of the film. By provision of the distributing layer 7, the highest possible concentration of liquid is achieved in the area under the film, at the same time as the distributing layer ensures that as great a surface area as possible has a high concentration of liquid. To ensure that saturation is achieved as quickly as possible in the distributing layer 7, the latter preferably has very small capillaries and is advantageously thin.

It will be noted that although the transport of liquid takes place in the manner described above, the lower layer is not emptied entirely of liquid but instead provides a moist environment for the wound bed, which is favourable as regards healing.

For the desired transport of liquid to take place from the wound bed to the second distributing layer 7, it is important that the various layers in the wound pad are in good contact with one another and that the vapour-permeable layer 8 is in good contact with the second distributing layer 7. For this purpose, the layer 3 is preferably fixed to the first distributing layer 5 by a thin layer of glue, for example an adhesive coating with a weight per unit area of 10 g/m$^2$. The layer 6 is air-laid on the first distributing layer 5 and/or the second distributing layer 7 and in this way has good contact with said layer/layers through mechanical bindings. It is possible to further increase the contact between the layers 5 and 6, 6 and 7 or 5, 6 and 7 by entangling or needling. It is also possible to ensure good contact with the aid of adhesive, heat and pressure or ultrasound, e.g. if the layer 6 is made of a foam material. The second distributing layer 7 is preferably fixed to the layer 6 and to the film 8 by means of thin layers of adhesive.

A method for achieving good contact between distributing layers 5, 7 of fibre material and the liquid-retaining and liquid-transporting layer 6 is one in which, during the air-laying of this layer, a thin layer of the fibres that are to form the distributing layer 5 or 7 is first air-laid, after which the various fibres that form the layer 6 are air-laid, and the air-laying is then completed with a thin layer of fibres that are to form the distributing layer 7 or 5, after which the various layers 5, 6 and 7 are bound together to form an integrated unit with the aid of heat and pressure, for example. It is of course conceivable to use this method to integrate only one of the distributing layers with the layer 6.

To ensure that liquid does not leak from the side edges of the layers 3-7 and run down, possibly back to the wound bed, the film can advantageously be tightly secured to these edges. The fact that the film 8 is vapour-permeable also permits evaporation of moisture on the skin in that part of the film extending peripherally outside the edges of the layers 3-7 of absorbent material, under the condition naturally that the adhesive coating 4 is also vapour-permeable in this area. To make it easier to secure the polymer film 8 to the layers 3-7, vacuum forming can be used to give it a three-dimensional shape corresponding to the shape of the layers. This preliminary shaping is advantageous even if the film is not secured adhesively to the edges of the layers 3-7.

Another way of preventing leakage is to weld the edges on the wound pad 2.

The polymer film 8 can be composed of a film of polyethylene, polyester, polytetrafluoroethylene or polyurethane, which is microporous or is in some other way made permeable to vapour. A vapour-permeable film is intended to mean that the plastic film, under normal conditions, allows vapour to pass through, but not liquid. The vapour permeability (WVTR: Water Vapour Transmission Rate) of the polymer film 8 must be greater than 2000 g/m$^2$ per 24 hours, measured by ASTM D 6701. The polymer film is preferably composed of a monolithic film, i.e. a film in which the vapour permeability increases markedly if the film is in contact with liquid. An example of such a film is Platilon® 2202 from Epurexs Films GmbH & Co KG, Bomlitz, Germany.

The dressing according to the invention is intended to remain in place on a wound for a period of several days without having to be changed. The healing process is facilitated by the fact that the wound is thus able to heal over a long period of time without interruption. A crucial factor in determining how long a dressing can be left in place on a seeping wound lies in the liquid handling capacity of the dressing. Liquid handling capacity means the amount of liquid that a dressing can take up from a wound before it stops functioning, i.e. can no longer absorb wound exudate released from the wound, which is manifested by leakage taking place. The liquid handling capacity is therefore dependent on the amount of liquid that can be stored in the dressing and on the amount of liquid evaporated. While the maximum amount of liquid that can be stored is not dependent on time, the amount of liquid that is evaporated is time-dependent and represents an important parameter in dressings that are intended to be used for a long period of time. By arranging a second distributing layer between the liquid-retaining and liquid-transporting layer and the polymer film, the evaporation is maximal over a large surface area as soon as liquid absorbed in the liquid-retaining and liquid-transporting layer reaches the top face of the latter. Moreover, the capillary force in the capillaries of the distributing layer is so great that the speed of transport of the liquid in the liquid-retaining and liquid-transporting layer 6 increases when liquid absorbed in this layer comes into contact with the capillaries in the second distributing layer 7. All in all, this means that a wet surface arises under the film 7 earlier than if the film were arranged directly against the liquid-retaining and liquid-transporting layer without an intermediate distributing layer. Thus, the present invention means that the vapour permeability of the polymer film 8 can be used in a better way than before, by virtue of the fact that the period of maximum evaporation increases considerably through the provision of a distributing layer between the polymer film and the liquid-retaining and liquid-transporting layer and thus also the amount of liquid that the dressing can handle during a defined period of time. For dressings that are designed to remain on a wound for a long period of time, the evaporation parameter is of great importance.

Moreover, the first distributing layer 5 has the effect that the lower layer 3 is drained more quickly, such that absorbed liquid quickly reaches the layer 6 and can be sucked up through the surface of said layer. This means that absorbed liquid quickly reaches the upper distributing layer.

Figure 2:
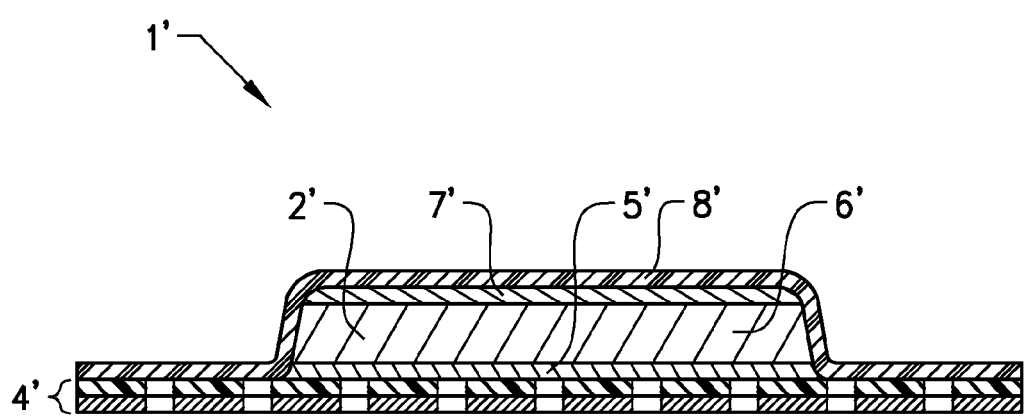
FIG. 2 shows a view, similar to FIG. 1, of a wound dressing according to a second preferred embodiment of the invention.

FIG. 2 shows a dressing 1' according to a second embodiment of the invention. The components of the dressing 1' that correspond to similar components in the dressing 1 according to FIG. 1 have been given the same reference numbers with addition of a prime symbol. The wound pad 2' is thus composed of a liquid-retaining and liquid-transporting layer 6' which is arranged between two distributing layers 5' and 7'. Liquid released from a wound is thus first absorbed in the distributing layer 5' and is spread across the surface thereof. Since the distributing layer is thin and has small capillaries, it quickly becomes saturated, and liquid absorbed in the distributing layer 5' quickly comes into contact with the liquid-transporting 6', which transports the liquid onwards to the second distributing layer 7', from which liquid evaporates through the vapour-permeable film 8'. Some of the liquid absorbed in the layer 6' will be stored in superabsorbent particles that are optionally present. When the storage capacity of the wound pad has been used to the maximum, i.e. when absorbent fibres and superabsorbents in the layer 6' are filled with liquid, the dressing can continue to function if the amount of liquid that can evaporate per unit of time is greater than or equal to the amount of liquid that is released from the wound bed.

The embodiments described can be modified without departing from the scope of the invention. For example, the various layers can have different surface areas, e.g. the upper layers can have a smaller surface area than the lower ones. Moreover, the layers in the wound pad can have a different shape than or the same shape as the vapour-permeable polymer film, e.g. rectangular or square with round corners, round, oval, etc. If the various layers in the wound dressing contain weldable constituents, they can be brought into tight contact with one another by welding with the aid of heat and pressure or with the aid of ultrasound. The vapour-permeable layer can be composed of a laminate of polymer film and nonwoven, preferably a hydrophobic nonwoven. The scope of the invention is therefore limited only by the content of the attached claims.

The invention claimed is:

1. A wound dressing comprising a wound pad and a layer of vapour-permeable material arranged on top of the wound pad and extending peripherally outside the wound pad, wherein at least that part of the vapour-permeable layer extending peripherally outside the wound pad is coated with an adhesive, and wherein the wound pad comprises a liquid-retaining and liquid-transporting layer, and an upper distributing layer and lower distributing layer which bear against the top and underside, respectively, of the liquid-retaining and liquid-transporting layer.

2. The wound dressing of claim 1, wherein the wound pad further comprises includes a liquid-transporting first layer, which is arranged under the lower distributing layer and bears thereon.

3. The wound dressing of claim 1, wherein the layers of the wound pad are connected adhesively or mechanically to one another, and the layer of vapour-permeable material is connected adhesively to the wound pad.

4. The wound dressing of claim 1, wherein the layers of the wound pad are connected to one another with the aid of heat and pressure or with the aid of ultrasound.

5. The wound dressing of claim 1, wherein the liquid-retaining and liquid-transporting layer comprises one or more plies comprising a mixture of hydrophilic or hydrophilized absorbent fibres and superabsorbents in powder form, fibre form or other form.

6. The wound dressing of claim 5, wherein the liquid-retaining and liquid-transporting layer further comprises binding fibres.

7. The wound dressing of claim 5, wherein the liquid-retaining and liquid-transporting layer has capillaries of different sizes, wherein the capillaries in contact with the upper distributing layer are smaller than the capillaries in other areas of the liquid-retaining and liquid-transporting layer.

8. The wound dressing of claim 5, wherein the proportion by weight of superabsorbents to absorbent fibres in the mixture of absorbent fibres and superabsorbents is greater in an upper part of the liquid-transporting and liquid-retaining layer than in a lower part thereof.

9. The wound dressing of claim 5, wherein at least one of the upper and lower distributing layers integrated in the liquid-retaining and liquid-transporting layer.

10. The wound dressing of claim 1, wherein the liquid-retaining and liquid-transporting layer comprises polymer foam with or without admixture of superabsorbents.

11. The wound dressing of claim 2, wherein the liquid-transporting first layer comprises a polymer foam.

12. The wound dressing of claim 1, wherein at least one of the upper and lower distributing layers comprises a tissue, a hydrophilic nonwoven material or polymer foam.

13. The wound dressing of claim 1, wherein the vapour-permeable layer comprises a polymer film that has a vapour permeability greater than 2000 $g/m^2$ per 24 hours, measured according to ASTM D 6701.

14. The wound dressing of claim 1, wherein the wound pad is coated on its underside with the adhesive.

15. The wound dressing of claim 14, wherein the adhesive comprises a silicone adhesive placed on a perforated support, which in turn is secured to the underside of the wound pad and to the vapour-permeable layer in the part thereof extending peripherally outside the wound pad.

16. The wound dressing of claim 14, wherein the adhesive is a liquid-permeable adhesive.

* * * * *

UNITED STATES PATENT AND TRADEMARK OFFICE
CERTIFICATE OF CORRECTION

PATENT NO. : 8,513,481 B2  
APPLICATION NO. : 13/378490  
DATED : August 20, 2013  
INVENTOR(S) : Gergely et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 10 days.

Signed and Sealed this

Fifteenth Day of September, 2015

Michelle K. Lee
*Director of the United States Patent and Trademark Office*